(12) United States Patent
Budny et al.

(10) Patent No.: US 6,830,745 B1
(45) Date of Patent: *Dec. 14, 2004

(54) COMPOSITIONS FOR TREATING BIOFILM

(75) Inventors: John A. Budny, Westlake Village, CA (US); Matthew J. Budny, Westlake Village, CA (US)

(73) Assignee: Pharmacal Biotechnologies, LLC, Westlake Village, CA (US)

(*) Notice: Subject to any disclaimer, the term of this patent is extended or adjusted under 35 U.S.C. 154(b) by 480 days.

This patent is subject to a terminal disclaimer.

(21) Appl. No.: 09/587,818

(22) Filed: Jun. 6, 2000

Related U.S. Application Data

(63) Continuation-in-part of application No. 09/249,674, filed on Feb. 12, 1999, now Pat. No. 6,159,447, which is a continuation-in-part of application No. 08/951,393, filed on Oct. 16, 1997, now Pat. No. 5,871,714.

(51) Int. Cl.$^7$ .......................... A61K 7/16; A61K 7/28; A61K 38/00; A61K 31/70
(52) U.S. Cl. .............. 424/49; 424/50; 514/2; 514/23
(58) Field of Search .................... 424/49, 50; 514/2, 514/23

(56) References Cited

U.S. PATENT DOCUMENTS

| | | | | |
|---|---|---|---|---|
| 4,138,476 A | * | 2/1979 | Simonson et al. | ............ 424/50 |
| 5,871,714 A | * | 2/1999 | Budny et al. | ................ 424/49 |
| 6,159,447 A | * | 12/2000 | Budny et al. | ................ 424/49 |

* cited by examiner

*Primary Examiner*—Kevin E. Weddington
(74) *Attorney, Agent, or Firm*—Colin P. Abrahams

(57) ABSTRACT

A two component composition comprises an anchor enzyme complex to degrade biofilm structures and a second anchor enzyme component having the capability to act directly upon the bacteria for a bactericidal effect.

17 Claims, 1 Drawing Sheet

COMPOSITIONS FOR TREATING BIOFILM

CROSS REFERENCE TO RELATED APPLICATIONS

This application is a continuation-in-part of U.S. application Ser. No. 09/249,674 filed Feb. 12, 1999 now U.S. Pat. No. 6,159,447, which is a continuation-in-part of U.S. application Ser. No. 08/951,393 filed Oct. 16, 1997 (issued as U.S. Pat. No. 5,871,714 on Feb. 16, 1999), both of which are incorporated herein by reference.

FIELD AND BACKGROUND OF THE INVENTION

Standard chemical analyses, traditional microscopic methods as well as digital imaging techniques such as confocal scanning laser microscopy, have transformed the structural and functional understanding of biofilms. Investigators, with these techniques have a clearer understanding of biofilm-associated microorganism cell morphology and cellular functions. The heightened awareness of metabolic biochemistry and the events associated with them have led to a better understanding, not only of individual cells and their varying environments, but also collections of cells that form colonies. Further, certain relationships of colonies to each other are under the direct influence of the biofilm in which they reside.

Concurrent with the increased understanding of cellular activity and inter-colony relationships, there has been an awareness developed about the biofilm in which the cells reside. While there has been an increased understanding of the architecture and composition of the biofilm matrix, the most significant advances have occurred in the inter-relationships among cells, colonies and biofilm matrices. Indeed, the basis of one aspect of this invention is founded in the integration of the enlightened understanding of microorganism activity within the influence of the biofilm in which they reside.

Biofilms are matrix-enclosed accumulations of microorganisms such as bacteria (with their associated bacteriophages), fungi, protozoa and viruses that may be associated with these elements. While biofilms are rarely composed of a single cell type, there are common circumstances where a particular cellular type predominates. The non-cellular components are diverse and may include carbohydrates, both simple and complex, proteins, including polypeptides, lipids and lipid complexes of sugars and proteins (lipopolysaccharides and lipoproteins).

For the most part, the unifying theme of non-cellular components of biofilms is its backbone. In virtually all known biofilms, the backbone structure is carbohydrate or polysaccharide-based. The polysaccharide backbone of biofilms serves as the primary structural component to which cells and debris attach. As the biofilm grows, expands and ages along biologic and non-biologic surfaces in well-orchestrated enzymatic synthetic steps, cells (planktonic) and non-cellular materials attach and become incorporated into the biofilm. The growing biofilm not only attracts living cells; it also captures debris, food particles, cell fragments, insoluble macromolecules and other materials that add to the layer upon the polysaccharide backbone. In this fashion, layering continues and is repeated so that the initial layers i.e., those closest to the original polysaccharide backbone, become buried or embedded in the biofilm. As the biofilm ages, there are layers upon layers of polysaccharide backbone with the attendant cells, debris and insoluble macromolecular structures.

Biofilms are the most important primitive structure in nature. In a medical sense, biofilms are important because the majority of infections that occur in animals are biofilm-based. Infections from planktonic bacteria, for example, are only a minor cause of infectious disease. In industrial settings, biofilms inhibit flow-through of fluids in pipes, clog water and other fluid systems and serve as reservoirs for pathogenic bacteria and fungi. Industrial biofilms are an important cause of economic inefficiency in industrial processing systems.

Biofilms are prophetic indicators of life-sustaining systems in higher life forms. The nutrient-rich, highly hydrated biofilms are not just layers of plankontic cells on a surface; rather, the cells that are part of a biofilm are a highly integrated "community" made up of colonies. The colonies, and the cells within them, express exchange of genetic material, distribute labor and have various levels of metabolic activity that benefits the biofilm as a whole.

Planktonic bacteria, which are metabolically active, are adsorbed onto a surface which has copious amounts of nutrients available for the initial colonization process. Once adsorbed onto a surface, the initial colonizing cells undergo phenotypic changes that alter many of their functional activities and metabolic paths. For example, at the time of adhesion, Pseudomonas aeruginosa (P. aeruginosa) shows upregulated algC, algD, algU etc. genes which control the production of phosphomanomutase and other pathway enzymes that are involved in alginate synthesis which is the exopolysaccharide that serves as the polysaccharide backbone for P. aeruginosa's biofilm. As a consequence of this phenotypic transformation, as many as 30 percent of the intracellular proteins are different between planktonic and sessile cells of the same species.

In summary, planktonic cells adsorb onto a surface, experience phenotypic transformations and form colonies. Once the colonizing cells become established, they secrete exopolysaccharides that serves as the backbone for the growing biofilm. While the core or backbone of the biofilm is derived from the cells themselves, other components e.g., lipids, proteins etc, over time, become part of the biofilm. Thus a biofilm is heterogeneous in its total composition, homogenous with respect to its backbone and heterogeneous with respect it its depth, creating diffusion gradients for materials and molecules that attempt to penetrate the biofilm structure.

Biofilm-associated or sessile cells predominate over their planktonic counterparts. Not only are sessile cells physiologically different from planktonic members of the same species, there is phenotypic variation within the sessile subsets or colonies. This variation is related to the distance a particular member is from the surface onto which the biofilm is attached. The more deeply a cell is embedded within a biofilm i.e., the closer a cell is to the solid surface to which the biofilm is attached or the more shielded or protected a cell is by the bulk of the biofilm matrix, the more metabolically inactive the cells are. The consequences of this variation and gradient create a true collection of communities where there is a distribution of labor, creating an efficient system with diverse functional traits.

Biofilm structures cause the reduced response of bacteria to antibiotics and the bactericidal consequences of antimicrobial and sanitizing agents. Antibiotic resistance and persistent infections that are refractory to treatments are a major problem in bacteriological transmissions, resistance to eradication and ultimately pathogenesis. While the consequences of bacterial resistance and bacterial recalcitrance are the same, there are two different mechanisms that explain the two processes.

The use of enzymes in degrading biofilms is not new. Compositional patents as well as published scientific literature support the concept of using enzymes to degrade, remove and destroy biofilms. However, the lack of consistency in results and the inability to retain the enzymes at the site where their action is required has prohibited their widespread use.

As an alternative to enzymes, harsh chemicals, elevated temperatures and vigorous abrasion procedures are preferentially used over enzymes. There are conditions, however, where these non-enzymatic approaches cannot be used e.g., caustic- and acidic-sensitive environments, temperature or abrasion sensitive components that are associated with the biofilm and dynamic fluid action. When a biofilm is growing in an area where there is a constant fluid flow, the agents that remove biofilms are flushed away before they can carry our their desired function. This is particularly true for medical situations where aggressive sterilization procedures cannot be carried out and there is a desired fluid flow.

Removing and controlling biofilm growth in biologic media are specifically sensitive to harsh treatments. Biofilms in the oral cavity, on implanted devices and infections that occur in the alimentary and vaginal tracts or in eyes, ears etc. are particularly suited for an enzymatic treatment. There are also specific disease conditions, such as pneumonia and cystic fibrosis which are bacteria-based and occur in the lung, that would benefit from an enzymatic treatment only if the enzymes could be retained at the site long enough to fully realize their therapeutic actions.

Biofilm growth and the proliferation of infections in biologic systems are particularly sensitive to fluid-flow dynamics. Specific organs where infections occur e.g. eyes, oral cavity, gastrointestinal tract, vaginal tract, lungs etc., fluid and mucus flow is an integral part of the system's normally functioning mode. Consequently, it is desirable to have the capability of removing unwanted biofilms in a non-harsh way in which the agent that acts on the biofilm is retained in close proximity to the biofilm and not swept away by fluids that are integral to the functioning system.

There are situations in or related to biologic systems where flow is minimal or non-existent. In these circumstances, the lack of demonstrated efficacy of enzymes to control biofilms is not related exclusively to their lack of ability to be retained at the site of the biofilm. Rather, the choice of enzyme to degrade the biofilm was inappropriate. An example is biofilm control on contact lenses and the cases or containers that hold the lenses when they are not in use. In these circumstances, it may not be a mandatory requirement for a means to retain the enzymes at or near the biofilm structure but only that the appropriate enzyme be part of the enclosed system.

It is also desirable to not only be able to degrade a biofilm within a biologic system, but also to be able to have a direct effect on the bacterial cells that are released as the biofilm is undergoing degradation. The combination of biofilm degradation and agents that directly affect bacterium is also not a new strategy. However, not infrequently in an open system, the same forces that flush or sweep away the biofilm degrading enzymes also flush bactericidal agents so that they cannot act directly upon bacteria unless there is a chance meeting between the agent and a planktonic bacterium.

SUMMARY OF THE INVENTION

Antibiotic/Antimicrobial Resistance. In the case of antibiotic or antimicrobial resistance, biofilms provide the unique opportunity for bacteria to reside in close proximity with one another for long periods of time. This prolonged juxtaposition of bacteria allows gene transfer between and among bacteria, allowing the genes of resistance to be transferred to same or different strains of bacteria to neighboring cells that are not resistant. Consequently, a virulent cell can transfer its virulence genes to a non-virulent cell, making it resistant to antibiotics.

Antibiotic/Antimicrobial Recalcitrance. In the case of antibiotic or antimicrobial recalcitrance, there are two possible explanations, both of which involve the biofilm and both of which may be operative simultaneously. While gene transfer may occur, it is not a factor in recalcitrance.

The first of the explanatory mechanisms is simply a physical phenomenon: the biofilm structures present a barrier to penetration of antibiotics and antimicrobial agents and a protective shroud to physical agents such as ultraviolet radiation. The biofilm, with its polysaccharide backbone and residual debris that is associated with the biofilm, provides a barrier to deep-seated bacteria. Unless the biofilm is removed or disrupted, complete cellular kill within the biofilm structure is not achieved by chemical or physical agents.

The second explanatory mechanism is based on biochemical or metabolic principles. Just as the deep-seated bacteria are protected from chemical and physical agents by the "barrier" effect of the biofilm, the biofilm also acts as a barrier to nutrients that are necessary for normal metabolic activity. Further, the nutrient-limited bacteria are in a reduced state of metabolic activity, which make them less susceptible to chemical and physical agents because the maximal effects of these killing agents are achieved only when the bacteria are in a metabolically active state.

With any of the possible mechanistic explanations for either resistance or recalcitrance, removal or disruption of the biofilm is a mandatory requirement. Stripping away of the biofilm components e.g., the polysaccharide backbone with the accumulated debris accomplishes several objectives: 1) reduced opportunity for gene transfer; 2) increased penetration of chemical and physical agents; and 3) increased free-flow of nutrients which would elevate the metabolic activity of the cells and make them more susceptible to chemical and physical agents. Furthermore, removal or disruption of the biofilm will free cells from a sessile state to make them planktonic which also increases their susceptibility to chemical and physical agents.

Prevention of Biofilm Formation. Under ideal conditions for controlling biofilms, the preferred approach for limiting the detrimental effects of biofilms is prevention of initial colonization by cells. For the most part, these approaches focus on the environment in which planktonic bacteria are present without particular attention to the bacteria themselves. This can be done to a limited extent through physical means e.g., electrical charges etc., chemical strategies e.g., surface coatings (paints and varnishes with antimicrobial chemicals) etc. and biochemical means e.g. nutrient limitation. However, for the majority of situations when fouling by biofilms occurs, these strategies are not practical or at best have limited utility.

Limiting Early Biofilm Growth. The next line of defense against the adverse effects of biofilms revolves around curtailing the consequences of the post-initial colonization of planktonic bacteria to a surface by limiting the initial proliferation of the biofilm. This can be accomplished, only to a limited extent, by continual disruption of early, immature biofilms or by inhibiting the biosynthesis of the structural exopolysaccharide backbone. Interdiction of early exopolysaccharide synthesis is usually achieved by macrolide antibiotics e.g., large ring lactones, erythromycin being one example. This later course of action constitutes a shift from an attempt to control the biofilm structure or environment to a direct action upon the living cells within the biofilm.

Destroying Established Biofilms. For established biofilms, with various levels of embedded cells, disruption, fragmentation and removal of the biofilm is necessary. This can be accomplished, under limited circumstances, with physical means e.g., abrasion methods, sonication, electrical charge stimulation, detergent and enzymatic. There are obvious drawbacks to any one method, precluding a universal method or approach. However, the common trait of all of these methods lies in their focus on the biofilm structure and not the living cells within the biofilm.

If, by any one of the methods, the structure of the biofilm is altered or disturbed, a secondary, complementary attack on the living cells within the biofilm can be made with antibiotics and antimicrobial agents.

An important aspect of the invention lies in two concepts, both of which may operate independently, but when combined, they effectively remove biofilms and prevent their reestablishment. The first of these is the removal of the biofilm structure in an orderly and controlled manner. The second concept is a specific consequence of removing the biofilm structure. During the removal or dismantling of the biofilm structure, especially the exopolysaccharide backbone, cells within the biofilm become more susceptible to the bactericidal action of antimicrobials, antibiotics, sanitizing agents and host immune responses. As the biofilm is removed, some cells within the biofilm are liberated and become planktonic; others, however, remain sessile but are more vulnerable to being killed because the protective quality of the biofilm is reduced.

One aspect of the invention consists of one or more hydrolytic enzyme(s) whose specificity includes its (their) ability to degrade exopolysaccharide backbone structure(s) of a biofilm produced by bacterial strain(s). Attached to the enzyme(s), either through chemical synthetic procedures or recombinant technology, are one or more moieties that have the capability of binding, either reversibly, in a non-covalently, or irreversibly (covalent bonded) to a surface near the biofilm or the biofilm itself. This aspect is directed at the degradation of the biofilm backbone structure.

Another aspect of the invention consists of two or more hydrolytic enzymes. One enzyme has the specificity to degrade the biofilm's exopolysaccharide backbone structure of a biofilm; at least one other enzyme is hydrolytic in nature, having the capability to degrade proteins, polypeptides, lipids, lipid complexes of sugars and proteins (lipopolysaccharides and lipoproteins). Attached to the enzymes, either individually or collectively as a single unit through chemical synthetic procedures or recombinant technology, are one or more moieties that have the capability of binding either reversibly, non-covalently, or irreversibly (covalent bonded) to a surface near the biofilm or the biofilm itself. This aspect is directed at the degradation and removal of the biofilm backbone structure along with any other materials that may be associated with the backbone, which collectively constitute the entire biofilm.

Still another aspect of the invention consists of two or more enzymes, wherein at least one enzyme has the capability of degrading a biofilm structure produced by a bacterial strain, or a mixed combination of various strains, and the other enzymes(s) has (have) the capability of acting directly upon the bacteria, causing lysis of the bacterial cell wall. One or more moieties are attached to the enzymes, forming either a single unit or multiple units. The moieties are attached to the enzymes either through chemical synthetic procedures or recombinant technology to give the enzyme moiety the capability of binding either reversibly, non-covalently, or irreversibly (covalent bonded) to a surface near the biofilm or the biofilm itself. The purpose of this multi-enzyme system is directed at the degradation and removal of the biofilm with the contemporaneous bactericidal consequences for bacteria that were embedded in the biofilm's structure.

A fourth aspect of the invention consists of two sets of enzymes, the first being one or more enzymes with the appropriate anchor attached to the enzyme(s) for the purpose of degrading the biofilm structure; the second set of enzymes are also connected to anchor molecules whose function is to generate active oxygen to directly attack and kill bacteria that are exposed during the process of the degradation and removal of the biofilm.

A fifth aspect of the invention consists of one or more enzyme complexes to degrade biofilm structures and a second component of one or more unbound or free non-enzymatic bactericidal components whose function is to kill newly exposed bacteria as the biofilm structure is removed. The non-enzymatic bactericidal agents include, but are not limited to, antimicrobial agents, antibiotics, sanitizing agents and host immune response elements.

The purpose of these various embodiments is to hold or retain the biofilm-degrading enzymes and bactericidal components in fluid-flow systems that are open, partially open or, at least not completely closed systems. Without the capability to keep the appropriate active agents at or near the biofilm structure, they may be swept away in the fluid flow.

The above five previously described aspects of the invention apply to open or partially open systems where there is fluid flow. However, there is also an additional embodiment for completely closed systems in which the enzyme or antibacterial agent may or may not have a binding moiety attached to.

A sixth aspect of the invention consists of one or more appropriately selected enzymes, not being connected to a binding moiety but limited by their ability to degrade a biofilm that is contained within such a closed system where there is minimal to no fluid flow.

DETAILED DESCRIPTION OF THE INVENTION

Figure 1:
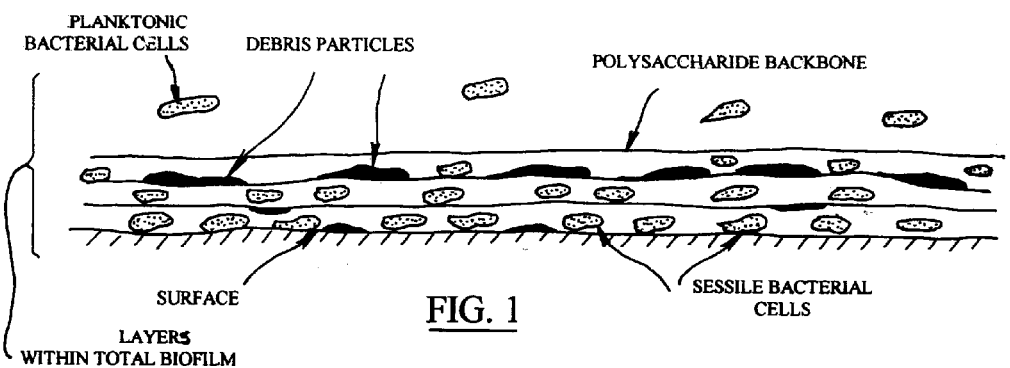
FIG. 1 is a schematic view of a biofilm from a distance.
Figure 2:
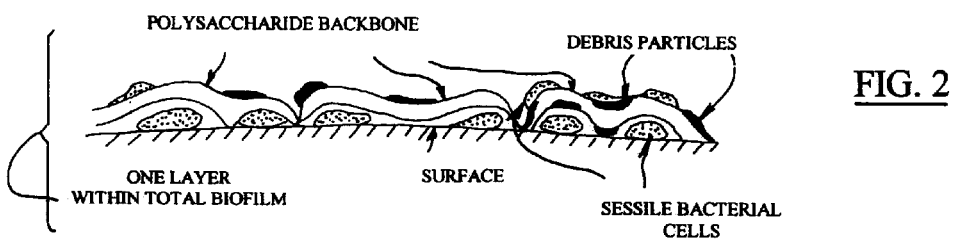
FIG. 2 is a schematic view showing the elements of a single layer within a biofilm structure.
Figure 3:
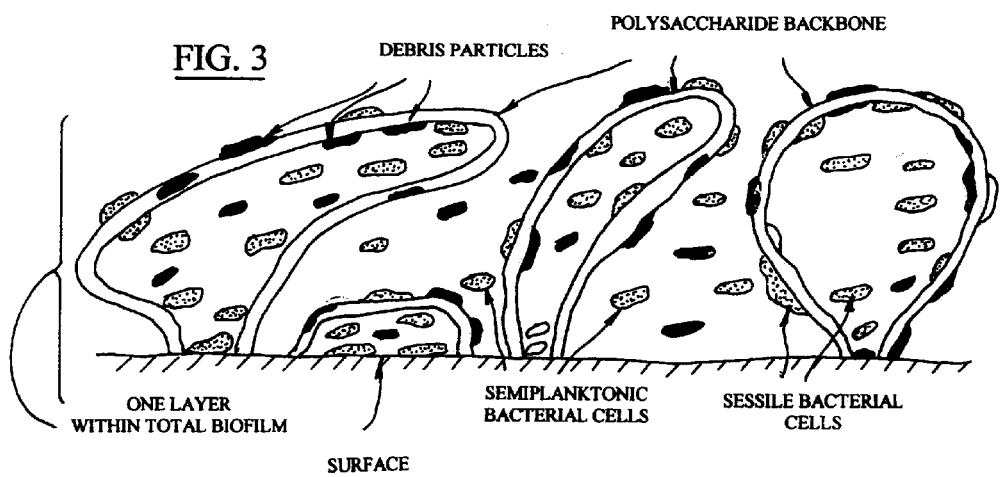
FIG. 3 is a schematic view of a magnified section of a single biofilm layer.
Figure 4:
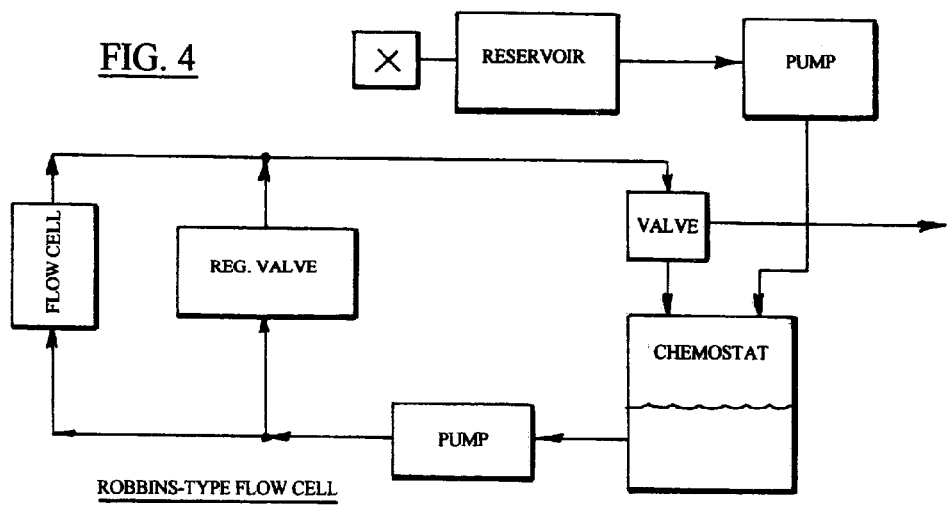
FIG. 4 is a diagram of a Robbins-type flow cell to measure biofilm dynamics under various flow conditions and components that may be added to the flowing fluid.

*P. aeruginosa*, which is a gram-negative rod, is one of many organisms found in slime residues associated with a wide variety of industrial, commercial and processing operations such as sewerage discharges, re-circulating water systems (cooling tower, air conditioning systems etc.), water condensate collections, paper pulping operations and, in general, any water bearing, handling, processing, collection etc. systems. Just as biofilms are ubiquitous in water handling systems, it is not surprising that *P. aeruginosa* is also found in association with these biofilms. In many cases, *P. aeruginosa* is the major microbial component.

In addition to its importance in industrial processes, *P. aeruginosa* and its associated biofilm structure has far-reaching medical implications, being the basis of many pathological conditions. *P. aeruginosa* is an opportunistic bacterium that is associated with a wide variety of infections. It has the ability to grow at temperatures higher than many other bacteria and it is readily transferred from an environmental setting to become host-dependent. Translocation, both within a specific medium and to other media, is facilitated with its single polar flagella giving it a velocity of 56 $\mu$m/sec mobility rate.

*P. aeruginosa* has nutritional versatility in being able to use a wide variety of substrates, fast growth rate, motility, temperature resiliency and short incubation periods all of which contribute to it predominance in natural microflora communities as well as being the cause of nosocomial (hospital acquired) infections.

Infections caused by *P. aeruginosa* begin usually with bacterial attachment to and colonization of mucosal and cutaneous tissues. The infection can proceed via extension to surrounding structures or infection may lead to bloodstream invasion, dissemination and sepsis syndrome.

Eye Infections. *P. aeruginosa* colonization in the eye leads to bacterial keratitis or corneal ulcer and endophthalmitis. Keratitis results from minor corneal injury, by which, the epithelial surface of the cornea is disrupted and allows bacterial access to the stroma. Contact lens use, particularly extended wear soft lenses, may exacerbate corneal ulcers. The lens itself or even the lens solution may introduce *P. aeruginosa* into the eye, while minor lens induced damage to the eye provides the opportunity of infection. Patients exposed to intensive care environment, have serious burns or have undergone ocular irradiation are especially susceptible to *P. aeruginosa* infections.

Endophthalmitis is a serious intra-ocular infection following perforation of the cornea, intra-ocular surgery or hematogenous spread of a previous *P. aeruginosa* infection.

Respiratory Infections. Alginate producing strains of *P. aeruginosa* infect the lower respiratory tract of patients with cystic fibrosis leading to acute and the chronic progression of the pathological condition. Primary pneumonia often presents bilateral bronchopneumonia with nodular infiltrates. Accompanying such infections are pleural effusions along with pathological progression leading to alveolar necrosis, focal hemorrhages and micro-abscesses.

Mucoid strains *P. aeruginosa* typically infect the lower respiratory tract of individuals with cystic fibrosis. Airway obstruction typically begins with bronchial infection and mucus production followed by colonization of *P. aeruginosa* in the lower respiratory tract. The colonization of *P. aeruginosa* accelerates disease pathology resulting in increased mucus production, airway obstruction, bronchiectasis and fibrosis in the lungs. These conditions eventually lead to pulmonary disease leading to hypertension and hypoxemia.

Ear Infections. *P. aeruginosa* is a common bacterium residing in the ear canal and is the primary pathogen causing external otitis. A *P. aeruginosa* infection in the ear canal may present a painful or itchy ear, purulent discharge in addition to the canal appearing edematous with detritus. *P. aeruginosa* is almost exclusively associated with malignant external otitis, an invasive condition, associated with diabetics, in which the infection spreads to surrounding soft tissue, cartilage and bone.

Urinary Tract Infections. *P. aeruginosa* is the most common causative agent in complicated and nosocomial urinary tract infections. Opportunities for infection occur during catheterization, surgery, obstruction and bloodborne transfer of *P. aeruginosa* to the urinary tract. As with other types of *P. aeruginosa* infections, urinary infections tend to be persistent, reoccurring, resistant to antibiotics and chromic in nature.

Skin and Soft Tissue Infections. *P. aeruginosa* can cause opportunistic infections in skin and soft tissue in locations where the integrity of the tissue is broken by trauma, burn injury, dermatitis and ulcers resulting from peripheral vascular disease. In the case of burn wounds, *P. aeruginosa*'s ability to infect is greatly enhanced due to the breakdown of the skin, antibiotic selection and burn-related immune defects.

More specifically, dressings for these types of wounds, as well as wounds in general where an infection can develop, the dressing can incorporate the appropriate enzymes that would degrade initial biofilm formation on these dressings. Such systems are closed systems or mostly so, and consequently, the enzymes may or may not have moieties attached to them as a means of retaining them to the would dressing. Further, an adjunct to the embodiment for this application there may also be associated with it suitable antimicrobial/antibiotic agents.

Endocarditis. *P. aeruginosa* has been shown to have a high affinity to cardiac tissue including heart valve tissue.

Alginate Biofilms of *P. aeruginosa*. At the root of *P. aeruginosa* initial colonization, as well as its proliferative growth rate, is the production of a mucoid exopolysaccharide layer comprised of alginate. This exopolysaccharide layer, along with lipopolysaccharide, protects the organism from direct antibody and complement mediated bactericidal mechanisms and from opsonophagocytosis. This protective biofilm allows *P. aeruginosa* to expand, grow and to exist in harsh environments that may exist outside the alginate biofilm. It is not surprising that the alginate biofilm is considered as an important virulence factor.

The alginate biofilm or "slime matrix" consists of a secreted exopolysaccharide that serves as the backbone structure of the biofilm. Alginate is a polysaccharide copolymer of $\beta$-D-mannuronic acid and $\alpha$-L-guluronic acid linked together by 1–4 linkages. The immediate precursor to the biosynthetic polymerization is guanosine 5'-diphosphate-mannuronic acid, which is converted to mannuronan. Post-polymerization of the mannuronan by acetylation at O-2 and O-3 and epimerization, principally at C-5, of some of the monomeric units to produce gulonate, results in varying degrees of acetylation and gulonate residues. Both the degree of acetylation and the percentage of mannuronic residues that have been converted to gulonate residues greatly affect the properties of the biofilm. For example, polymers rich in gulonate residues and in the presence of calcium, tend to be more rigid and stiff than polymers with low levels of gulonate monomeric units.

Construction of Anchor-Enzyme Complexes.

The Anchor Enzyme Complex can be constructed using chemical synthetic techniques. Additionally, the Anchor-Enzyme Complex, if the anchor is a polypeptide or protein, such as protein binding domains, lectins, selecting, heparin binding domains etc., can be constructed using recombinant genetic engineering techniques.

Types of Anchors.

Elastase binding domain for alginate

1. Carbohydrate and polysaccharide binding domains

2. Lectins
3. Selectins
4. Heparin binding domains
5. Additional anchors listed in U.S. Pat. No. 5,871,714, for example at column 8 lines 18–67, column 9 lines 1–5.

Type of Enzymes

1. Generally, enzymes in the class EC 4.2.2._, which are polysaccharide lyases:

| | |
|---|---|
| EC 3.1.2 | Glycoside Hydrolases, Galactoaminidases, Galactosidases, Glucosaminidases, Glucosidases, Mannosidases |
| EC 3.1.2.18 | Neuraminidase |
| EC 3.2._ | Dextranase, Mutanase, Mucinase, Amylase, Fructanase, Galactosidase, Muramidase, Levanase, Neuraminidase |
| EC 3.2.1.20 | α-Glucosidases |
| EC 3.2.1.21 | β-Glucosidase |
| EC 3.2.1.22 | α-Glucosidase |
| EC 3.2.1.25 | β-D-Mannosidase |
| EC 3.2.1.30 | Acetylglucosaminidase |
| EC 3.2.1.35 | Hyaluronoglucosaminidase |
| EC 3.2.1.51 | α-L-Eucosidase |
| EC 4.2.2.1 | Hyaluronate Lyase |
| EC 4.2.2.2 | Pectate Lyase |
| EC 4.2.2.3 | Alginate Lyase [Poly(β-D-Mannuronate) Lyase] |
| EC 4.2.2.4 | Chondroitin ABC Lyase |
| EC 4.2.2.5 | Chondroitin AC Lyase |
| EC 4.2.2.6 | Oligogalacturonide Lyase |
| EC 4.2.2.7 | Heparin Lyase |
| EC 4.2.2.8 | Heparan Lyase [Heparitin-Sulfate Lyase] |
| EC 4.2.2.9 | Exopolygalacturonate Lyase |
| EC 4.2.2.10 | Pectin Lyase |
| EC 4.2.2.11 | Poly (α-L-Guluronate) Lyase |
| EC 4.2.2.12 | Xanthan Lyase |
| EC 4.2.2.13 | Exo-(1,4)-α-D-Glucan Lyase | for degrading the polysaccharide backbone structure of biofilms.

2. Enzymes for removing debris embedded within the biofilm structure. These include many EC sub-classes with the general class of hydrolytic and digestive enzymes. In descriptive terms, they include enzymes that facilitate the breaking of chemical bonds and include the following:

Esterases—cleavage of ester bonds;

Glycolytic—cleavage of bonds found in oligo- and polysaccharides

Peptidases—cleavage of peptide bonds where the substrate is a protein or polypeptide;

Carbon-nitrogen cleavage—where the substrate is not a protein or polypeptide;

Acid anhydride cleaving enzymes;

Carbon-carbon bond cleavage;

Halide bond cleavage;

Phosphorus-nitrogen bond cleavage;

Sulfur-nitrogen bond cleavage; and

Carbon-phosphorus bond cleavage.

Typical examples include the following enzymes:

| | |
|---|---|
| EC 3.4._ | Endopeptidases; Peptide Hydrolases |
| EC 3.4.11 | Aminopeptidases |
| EC 3.4.11.5 | Propyl Aminopeptidases |
| EC 3.4.14 | Glycylpropyl Dipeptidases; Dipeptidyl Peptidase |
| EC 3.4.21 | Serine Endopeptidases |
| EC 3.4.21.1 | Chymotrypsin |
| EC 3.4.21.4 | Trypsin |
| EC 3.5._ | Amidohydrolases |

-continued

| | |
|---|---|
| EC 3.5.1.25 | N-Acetylglucosamine-6-phosphate Deacetylase |
| EC 4.1.3 | Oxo-Acid Lyases |
| EC 4.1.3.3 | N-Acetylmuraminate Lyases |
| EC 5.1.3_ | Carbohydrate Epimerases |
| EC 5.3.1.10 | Glucosamine-6-phosphate Isomerases |

Types of Bactericidal Agents

1. Enzymatic

A. Generation of Active Oxygen. Any member from the class of oxido-reductases, EC 1._ that generate active oxygen; Monosasccharide oxidases, Peroxidases, Lactoperoxidases, Salivary peroxidases, Myeloperoxidases, Phenol oxidase, Cytochrome oxidase, Dioxygenases, Monooxygenases B. Bacterial cell lytic enzymes Lysozyme, Lactoferrin 2. Non-Enzymatic A. Antimicrobial e.g., chlorhexidine, amine fluoride compounds, fluoride ions, hypochlorite, quaternary ammonium compounds e.g. cetylpyridinium chloride, hydrogen peroxide, monochloramine, providone iodine, any recognized sanitizing agent or oxidative agent and biocides.

B. Antibiotics. Including, but not limited to the following classes and members within a class:

Aminoglycosides

Gentamicin, Tobramycin, Netilmicin, Amikacin, Kanamycin, Streptomycin, Neomycin

Quinolones/Fluoroquinolones

Nalidixic Acid, Cinoxacin, Norfloxacin, Ciprofloxacin, Perfloxacin, Ofloxacin, Enoxacin, Fleroxacin, Levofloxacin Antipseudomonal Carbenicillin, Carbenicillin Indanyl, Ticarcillin, Azlocillin, Mezlocillin, Piperacillin Cephalosporins First Generation Cephalothin, Cephaprin, Cephalexin, Cephradine, Cefadroxil, Cefazolin Second Generation Cefamandole, Cefoxitin, Cefaclor, Cefuroxime, Cefotetan, Ceforanide, Cefuroxine Axetil, Cefonicid Third Generation Cefotaxime, Moxalactam, Ceftizoxime, Ceftriaxone, Cefoperazone, Cftazidime Other Cephalosporins Cephaloridine, Cefsulodin Other β-Lactam Antibiotics Imipenem, Aztreonam β-Lactamase Inhibitors Clavulanic Acid, Augmentin, Sulbactam Sulfonamides Sulfanilamide, Sulfamethoxazole, Sulfacetamide, Sulfadiazine, Sulfisoxazole, Sulfacytine, Sulfadoxine, Mafenide, p-Aminobenzoic Acid, Trimethoprim-Sulfamethoxazole Urinary Tract Antiseptics Methenamine, Nitrofurantoin, Phenazopyridine and other napthpyridines Penicillins Penicillin G and Penicillin V Penicillinase Resistant Methicillin, Nafcillin, Oxacillin, Cloxacillin, Dicloxacillin Penicillins for Gram-Negative/Amino Penicillins
    Ampicillin (Polymycin), Amoxicillin, Cyclacillin, Bacampicillin
Tetracyclines
    Tetracycline, Chlortetracycline, Demeclocycline, Methacycline, Doxycycline, Minocycline
Other Antibiotics
    Chloramphenicol (Chlormycetin), Erythromycin, Lincomycin, Clindamycin, Spectinomycin, Polymyxin B (Colistin), Vancomycin, Bacitracin
Tuberculosis Drugs
    Isoniazid, Rifampin, Ethambutol, Pyrazinamide, Ethinoamide, Aminosalicylic Acid, Cycloserine
Anti-Fungal Agents
    Amphotericin B, Cyclosporine, Flucytosine
Imidazoles and Triazoles
    Ketoconazole, Miconazaole, Itraconazole, Fluconazole, Griseofulvin
Topical Anti Fungal Agents
    Clotrimazole, Econazole, Miconazole, Terconazole, Butoconazole, Oxiconazole, Sulconazole, Ciclopirox Olamine, Haloprogin, Tolnaftate, Naftifine, Polyene, Amphotericin B, Natamycin

EXAMPLE

Since *P. aeruginosa* is a ubiquitous bacterial strain, found not only in the environment and in industrial settings where fouling occurs, but also in many disease conditions, it will serve as an example to illustrate the principles of the invention. Further, while there are many disease conditions for which *P. aeruginosa* is the cause, ocular infections will exemplify the implementation of the invention. The choice of *P. aeruginosa* as the biofilm-producing bacteria and pathogen and ocular infection as a consequence of the biofilm is not meant to preclude or limit the scope of this invention. The principles outlined in this example readily apply to all biofilms, whether produced by bacteria or other organisms, all biofilms that are generated by organisms and the embodiments, taken and implemented either individually or collectively.

*P. aeruginosa* is an opportunistic bacterial species, which once colonized at a site such as ocular tissue, produces a biofilm with a polysaccharide-based alginate polymer. This exopolysaccharide or glycocalyx matrix is the confine in which the bacterial species can grow and proliferate. This biofilm matrix can also serve as a medium for other, pathogenic bacteria, fungi and viruses. It is of therapeutic benefit, therefore, to remove the biofilm structure and eliminate all bacteria at the site, not only *P. aeruginosa*.

Alginate lyase, the expression product from the algL gene, can be obtained from various bacterial sources e.g. *Azotobacter vinelandii*, Pseudomonas syringe, *Pseudomonas aeruginosa* etc., producing an enzyme AlgL, which degrades alginate. Other genes, e.g. alxM, also provide a wide variety of alginate lyase and polysaccharide depolymerase enzymes with degrade alginate by various mechanisms.

Endogenous lectins, heparin binding domains and various receptors from animals and plants have receptors that bind to alginate. These receptors, when located on host cell surfaces, allow the evolving alginate biofilm to be retained by the infected tissue. Elastase (Leukocyte Elastase, EC 3.4.21.37 and Pancreatic Elastase, EC 3.4.21.36), which is a digestive enzyme, also has a domain that binds to alginate. Such binding capability, along with the degradative ability of the catalytic site in elastase, has been implicated in tissue degradation associated with alginate biofilm infections such as cystic fibrosis. In addition, other serine proteases also have alginate binding domains.

In one aspect of the invention, a fusion protein is created, using standard genetic engineering techniques. One of the traits or elements of the fusion protein is the ability to degrade alginate and a second property being a binding capability of the newly-created fusion protein, derived from, for example, the binding domain of elastase. The bi-functional protein fulfills the criteria set out in the invention in that the binding domain derived from elastase serves as the anchor and the alginate lyase portion of the fusion protein serves as the degradative enzyme for the biofilm.

This embodiment can be used to degrade alginate-based biofilms in industrial processes where fouling occurs, or implanted medical devices, including catheters and cannulae. This embodiment can also be used for a wide variety of infections such as: ophthalmic applications (infections, implants, contact lenses, surgical manipulations etc.), respiratory infections, including pneumonia and cystic fibrosis, ear infections, urinary tract infections, skin and soft tissue infections, infections that occur in burn victims, endocarditis, vaginal infections, gastrointestinal tract infections where biofilms, either impair function or cause infections and in disease conditions, such as cystic fibrosis.

It is within the scope of this invention that the principles outlined here also apply to all biofilms in all circumstances in which they occur.

Assay Procedure for Synthesized Anchor Enzyme Complexes

Preparation of Bacterial Biofilms. There are many procedures to prepare bacterial biofilms. Herein is one of those procedures.

The appropriate bacterial strain, or mixed strains if more than one strain is used, is incubated in tryptic soy broth for 18 to 24 hours at 37° C. After the incubation period, the cells are washed three times with isotonic saline and re-suspended in isotonic saline to a density of 106 CFU/ml. The re-suspended cells are incubated a second time with Teflon squares (1×1 cm) with a thickness of 0.3 cm for six to seven days at 37° C. The recovered cells in the saline incubation medium are planktonic bacteria, while those associated with the Teflon squares and the biofilm are sessile cells.

The biofilm-associated sessile cells are then treated with appropriate anchor-enzyme complexes that degrade the generated biofilm at various concentrations with or without bactericidal agents in either a completely closed system or an open system (flow-through chamber or cell). The bactericidal agent can be either an anchor enzyme system that generates active oxygen or a non-enzymatic, chemical that is a recognized antimicrobial agent, biocide or antibiotic.

Analysis of a Completely Closed System. The Teflon squares with the associated biofilm are transferred to isotonic saline medium containing a given concentration of anchor-enzyme complex that degrades the biofilm. At intervals of 3, 6, 12, 24 and 48 hours, the individual Teflon squares are washed three times with isotonic saline and finally added to fresh isotonic saline which is vigorously shaken or sonicated for tow minutes. The suspended mixture is diluted and counted for cell density and expressed as number of CFU/ml.

The same counting procedure can be used for the incubation medium.

Bactericidal agents are also incorporated into the experimental design, which also uses the same cell counting procedure.

Estimating Biofilm Size. At the end of any of the incubation steps, the biofilm can be recovered, dehydrated and weighed to obtain total biomass of the biofilm. Alternatively, the amount of alginate backbone can be determined where the biofilm contains Pseudomonas sp.

Extraction of Polysaccharide Backbone. After the second incubation and disruption of the biofilm, the bacterial cells are removed from the dispersion. With an increasing concentration of an ethanol/soling gradient, the alginate is precipitated, collected and washed three times with 95% ethanol. The precipitate is desiccated after which the quantity can be determined gravimetrically or by any number of chemical, enzymatic or combination of chemical and enzymatic methods. The most widely used method is the chemical method of which there are three types: uronic acid assay, orcinol-$FeCl_3$ and decarboxylation and $CO_2$ measurement.

Analysis in an Open System (Complete or Partial). The most widely used dynamic flow system that can be regulated from a completely closed to a completely open system is the Robbins Device or the Modified Robbins Device. The Modified Robbins Device allows the assessment of biofilms in which the fluid flow and growth rates of the biofilm can be regulated independently and simultaneously. A Robbins-type flow cell can be a completely closed system that possesses flow dynamics for assessing efficacy of anchor-enzyme complexes.

What is claimed is:

1. A two component composition comprising a first anchor enzyme complex to degrade biofilm structures and a second anchor enzyme complex having the capability to act directly upon bacteria for a bactericidal effect.

2. A composition as claimed in claim 1 wherein the first anchor enzyme complex contains alginate lyase to degrade the biofilm.

3. A composition as claimed in claim 1 wherein the first anchor enzyme complex contains an alginate binding domain.

4. A composition as claimed in claim 3 wherein the alginate binding domain is derived from elastase.

5. A composition as claimed in claim 1 wherein at least one of the first and second anchor enzyme complexes is a fusion protein.

6. A composition as claimed in claim 1 wherein the second anchor enzyme complex comprises lysozyme to lyse bacteria within the biofilm.

7. A composition as claimed in claim 1 wherein the second anchor enzyme complex comprises lactoferrin.

8. A composition as claimed in claim 1 wherein the second anchor enzyme complex comprises oxido-reductase enzymes that generate active oxygen for the purpose of killing bacteria within the biofilm.

9. A composition as claimed in claim 1 wherein the second anchor enzyme complex comprises hexose oxidase for the purpose of generating active oxygen.

10. A composition as claimed in claim 1 wherein the second anchor enzyme complex comprises lactoperoxidase for the purpose of generating active oxygen.

11. A composition as claimed in claim 1 wherein the second anchor enzyme complex comprises myeloperoxidase for the purpose of generating active oxygen.

12. A composition as claimed in claim 5 wherein the anchor of the first or second anchor enzyme complex is an alginate binding domain and whose catalytic part is alginate lyase.

13. A composition as claimed in claim 1 further comprising an antimicrobial/antibiotic.

14. A composition as claimed in claim 13 wherein the antimicrobial/antibiotic has a moiety connected to it so that the antimicrobial/antibiotic agent can be retained at a specific location within a closed system.

15. A composition as claimed in claim 1 wherein the first or second anchor enzyme complex further comprises one or more enzymes that have one or more moieties connected to them so that the anchor-enzyme can be retained at a specific location within a closed system.

16. A composition as claimed in claim 1 wherein the second anchor enzyme complex contains an alginate binding domain.

17. A method of degrading and/or removing biofilm comprising forming a first anchor enzyme complex for degrading a biofilm structure and adding thereto to form a two component composition a second anchor enzyme complex having a bactericidal effect, and introducing the two component composition to a site containing biofilm or susceptible to biofilm buildup.

* * * * *